United States Patent
Suzuki et al.

(10) Patent No.: US 12,402,779 B2
(45) Date of Patent: Sep. 2, 2025

(54) ENDOSCOPE AND ENDOSCOPE SYSTEM

(71) Applicant: OLYMPUS CORPORATION, Tokyo (JP)

(72) Inventors: Takuji Suzuki, Hachioji (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 377 days.

(21) Appl. No.: 17/897,610

(22) Filed: Aug. 29, 2022

(65) Prior Publication Data

US 2022/0409022 A1    Dec. 29, 2022

Related U.S. Application Data

(63) Continuation of application No. PCT/JP2020/009256, filed on Mar. 4, 2020.

(51) Int. Cl.
*A61B 1/00* (2006.01)
*A61B 1/018* (2006.01)
*A61B 1/06* (2006.01)

(52) U.S. Cl.
CPC ...... *A61B 1/00096* (2013.01); *A61B 1/00009* (2013.01); *A61B 1/00091* (2013.01); *A61B 1/018* (2013.01); *A61B 1/0676* (2013.01)

(58) Field of Classification Search
CPC ............ A61B 1/00096; A61B 1/00009; A61B 1/00091; A61B 1/018; A61B 1/0676;
(Continued)

(56) References Cited

U.S. PATENT DOCUMENTS

2008/0051628 A1* 2/2008 Pecherer ................ A61B 1/267
　　　　　　　　　　　　　　　　　　　　　600/112
2012/0289858 A1* 11/2012 Ouyang ............ A61B 1/00101
　　　　　　　　　　　　　　　　　　　　　600/562

(Continued)

FOREIGN PATENT DOCUMENTS

JP　　H03-51032 A　　3/1991
JP　　H06-54799 A　　3/1994
(Continued)

OTHER PUBLICATIONS

International Search Report dated May 26, 2020 received in PCT/JP2020/009256.

*Primary Examiner* — Anh Tuan T Nguyen
*Assistant Examiner* — James Edward Boice
(74) *Attorney, Agent, or Firm* — Scully, Scott, Murphy & Presser, P.C.

(57) ABSTRACT

An endoscope includes, in a distal end frame constituting a distal end portion, an objective optical unit including a voice coil motor that moves a moving lens frame forward and backward in a direction of an optical axis by using a plurality of magnets arranged on a periphery of the moving lens frame, and a plurality of internal components made of magnetic material and arranged around the objective optical unit. At least one of the internal components is arranged at a position where at least a part thereof intersects one of straight lines each connecting an extreme point of one of valleys of a specific isomagnetic line of magnetic fields formed by the magnets and one of two inflection points of the specific isomagnetic line, the two inflection points being located, with the one of the valleys positioned between the two inflection points.

17 Claims, 7 Drawing Sheets

(58) Field of Classification Search
CPC .......... A61B 1/051; A61B 1/07; A61B 1/015;
A61B 1/00188; G02B 23/2438
USPC ...................................................... 600/104
See application file for complete search history.

(56) References Cited

U.S. PATENT DOCUMENTS

| | | | |
|---|---|---|---|
| 2016/0213239 A1* | 7/2016 | Fujii | A61B 1/00163 |
| 2017/0258303 A1* | 9/2017 | Iguchi | G02B 7/09 |
| 2018/0031800 A1 | 2/2018 | Iguchi et al. | |
| 2019/0090727 A1* | 3/2019 | Shelton | A61B 1/00071 |
| 2019/0090729 A1* | 3/2019 | Sugiura | A61B 1/00096 |

FOREIGN PATENT DOCUMENTS

| | | |
|---|---|---|
| JP | 2000-051141 A | 2/2000 |
| JP | 2000-135198 A | 5/2000 |
| JP | 2009-142440 A | 7/2009 |
| JP | 2015-112336 A | 6/2015 |
| JP | 2015-114651 A | 6/2015 |
| WO | 2016/166855 A1 | 10/2016 |

* cited by examiner

ENDOSCOPE AND ENDOSCOPE SYSTEM

CROSS-REFERENCE TO RELATED APPLICATION

This application is a continuation application of PCT/JP2020/009256 filed on Mar. 4, 2020, the entire contents of which are incorporated herein by this reference.

BACKGROUND OF THE INVENTION

1. Field of the Invention

The present invention relates to an endoscope and an endoscope system that change an optical characteristic of an objective optical system by moving a movable frame by using an electromagnetic actuator.

2. Description of the Related Art

Conventionally, in a field of endoscopes, an endoscope capable of changing an optical characteristic of an objective optical unit provided in a distal end portion of the endoscope by moving a moving lens frame forward and backward in a direction of an optical axis has been proposed and put into practical use.

As an example of an objective optical unit of the endoscope of this type, Japanese Patent Application Laid-Open Publication No. 2015-114651 discloses an optical unit including: a cylindrical fixed portion (fixed frame); a cylindrical movable frame (movable portion) arranged inside the fixed frame; and a voice coil motor capable of relatively moving the movable frame in a direction of an optical axis with respect to the fixed frame by using a coil arranged in the fixed frame and magnets arranged in the movable frame.

In general, in the voice coil motor, the arrangement, the magnetic fields, and the like of the respective magnets are adjusted in order to enable the movable frame to be operated properly in the objective optical unit alone.

SUMMARY OF THE INVENTION

An endoscope according to one aspect of the present invention includes: an objective optical unit including an actuator, the actuator being configured to move a movable frame forward and backward in a direction of an optical axis by using a plurality of magnets; and a plurality of internal components made of magnetic material and arranged around the objective optical unit, the objective optical unit and the plurality of internal components being held in a distal end frame constituting a distal end portion of an insertion portion of the endoscope. At least one of the plurality of internal components is arranged at a position where at least a part of the at least one of the plurality of internal components intersects one of straight lines each connecting an extreme point of one of valleys of a specific isomagnetic line of magnetic fields formed by the plurality of magnets and one of two inflection points of the specific isomagnetic line, the two inflection points being located, with the one of the valleys positioned between the two inflection points.

An endoscope according to another aspect of the present invention includes: an objective optical unit including an actuator, the actuator being configured to move a movable frame forward and backward in a direction of an optical axis by using a plurality of magnets; and a plurality of internal components made of magnetic material and arranged around the objective optical unit, the objective optical unit and the plurality of internal components being held in a distal end frame constituting a distal end portion of an insertion portion of the endoscope. At least one of the plurality of internal components is arranged at a position where at least a part of the at least one of the plurality of internal components intersects one of lines each connecting extreme points of valleys of isomagnetic lines indicating different magnetic flux densities of magnetic fields formed by the plurality of magnets.

In addition, an endoscope system according to one aspect of the present invention includes the endoscope and an image processing apparatus configured to covert an image pickup signal, which is obtained by image pickup by the endoscope, into an image signal.

DETAILED DESCRIPTION OF THE PREFERRED EMBODIMENT(S)

Hereinafter, an embodiment of the present invention will be described with reference to drawings. The drawings relate to one embodiment of the present invention and FIG. 1 is a schematic configuration view of an endoscope system.

Figure 1:
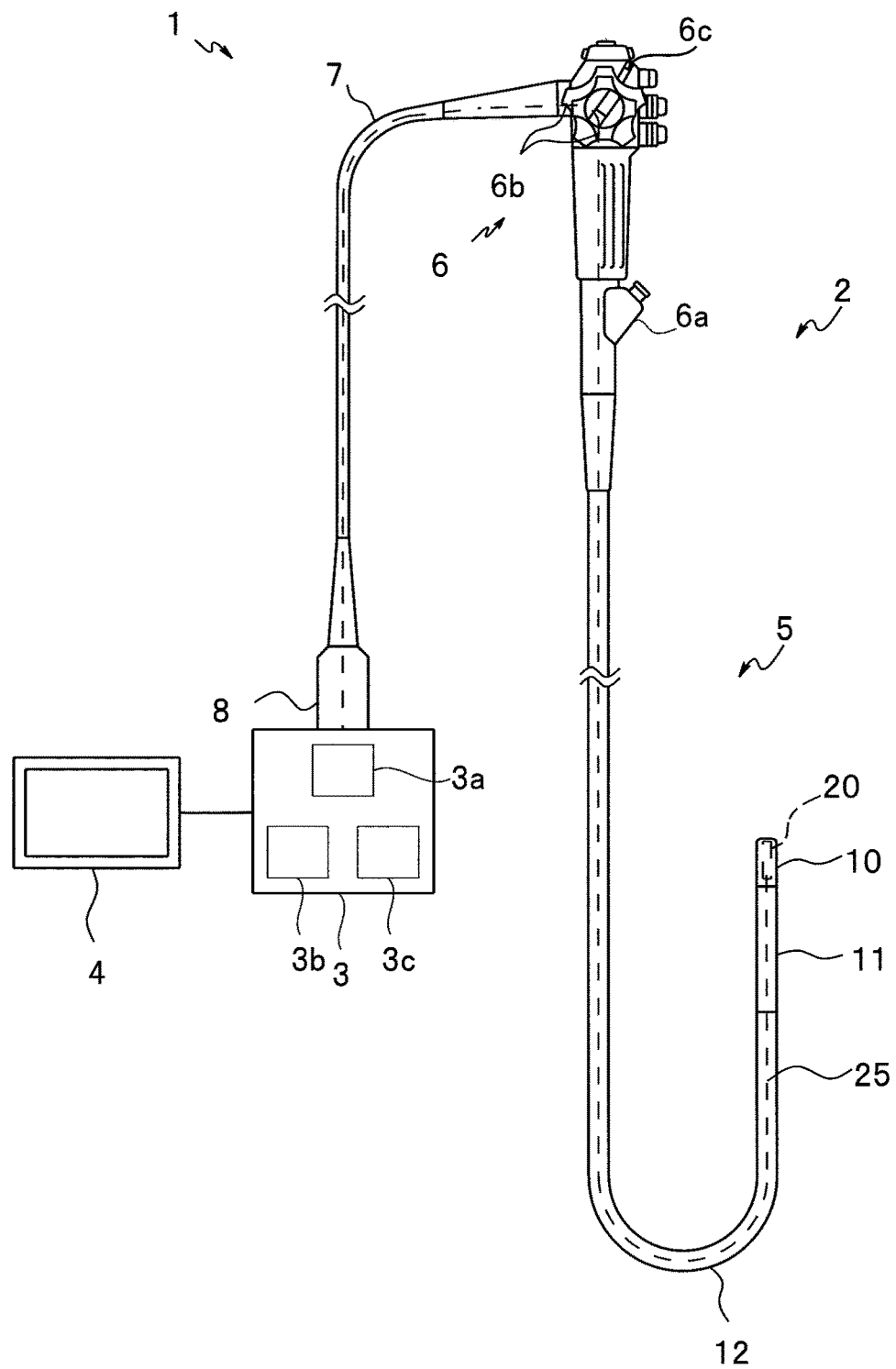
FIG. 1 is a schematic configuration view of an endoscope system.

An endoscope system 1 shown in FIG. 1 includes an endoscope 2, a control apparatus 3, and a display apparatus 4.

The endoscope 2 is configured to be insertable into a subject such as a human body, and to optically observe a predetermined observation site in the subject. Note that the subject into which the endoscope 2 is inserted is not limited to a human body, but may be another living body, or an artificial object such as a machine, a structure, etc.

The endoscope 2 includes an insertion portion 5 configured to be inserted into a subject, an operation portion 6 provided continuously with a proximal end side of the insertion portion 5, and a universal cord 7 extended from the operation portion 6.

The insertion portion 5 includes, in the following order from the distal end side toward the proximal end side, a distal end portion 10, a bending portion 11 configured to be bendable, and a flexible tube portion 12 having flexibility.

Figure 2:
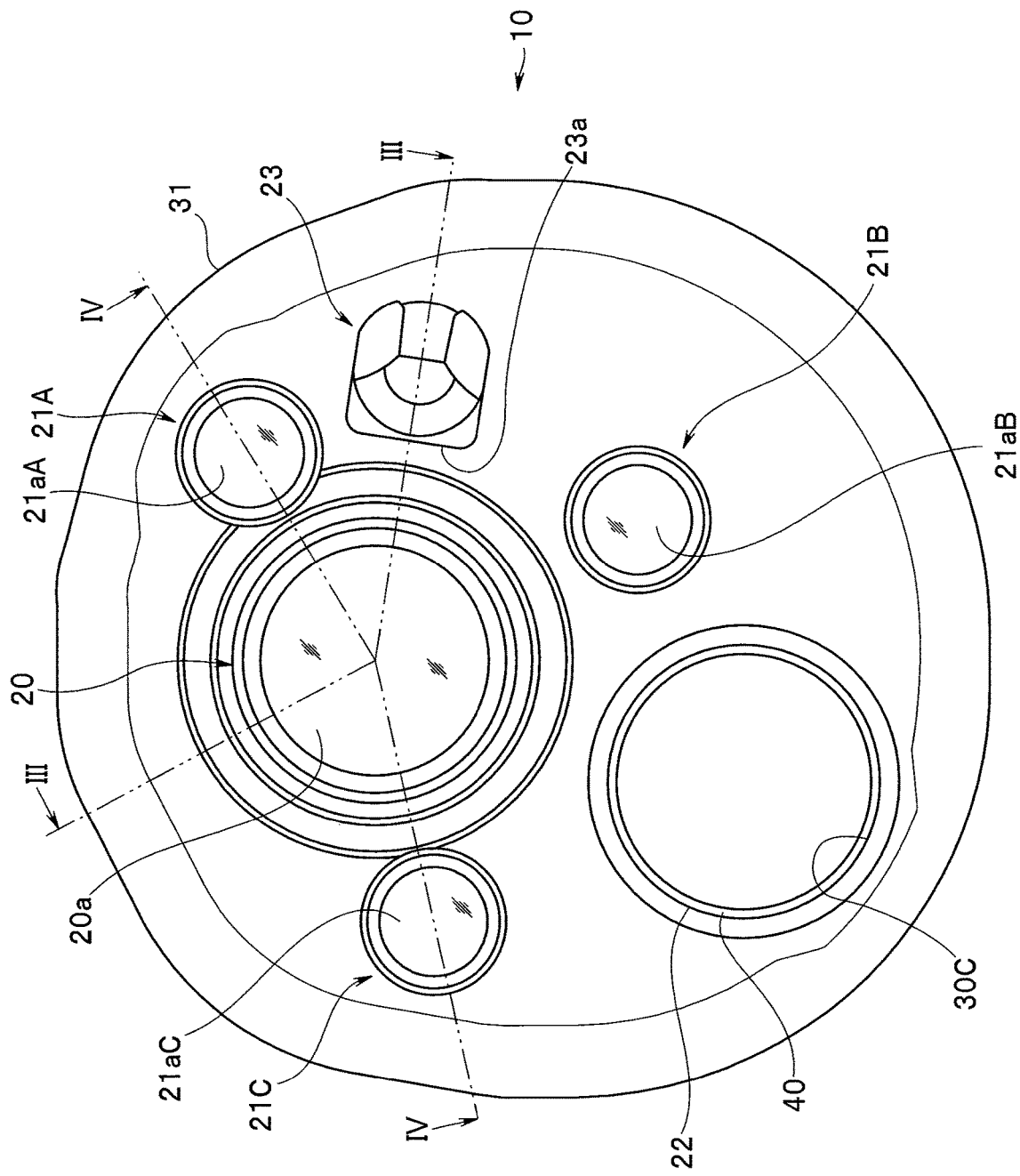
FIG. 2 is a view of an end surface of a distal end portion.

Although details will be described later, as shown in FIG. 2, the distal end portion 10 is provided with: an image pickup unit 20 configured to form an image of a subject on an image pickup device; a plurality of illumination optical units (for example, three illumination optical units: first to third illumination optical units 21A to 21C); a treatment instrument channel port 22; and a gas/liquid feeding nozzle 23.

Figure 5:
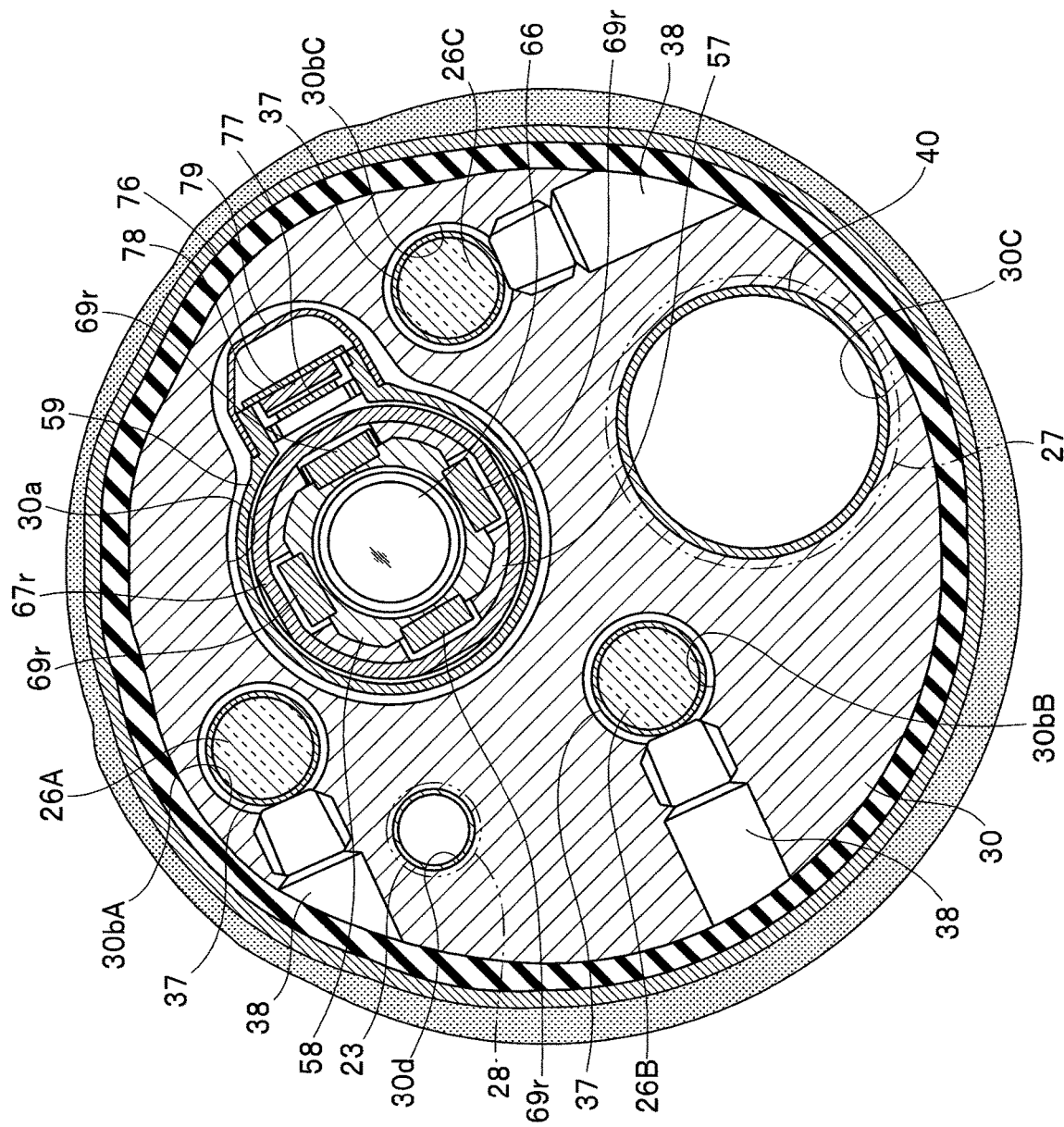
FIG. 5 is a sectional view taken along the line V-V in FIG. 3.

A composite cable 25 for transmitting and receiving various signals is connected to the image pickup unit 20 (see FIG. 1). Further, as shown in FIG. 5, first to third light guide bundles 26A to 26C are connected respectively to the first to third illumination optical units 21A to 21C. Furthermore, a treatment instrument channel 27 is connected to the treatment instrument channel port 22. Furthermore, a gas/liquid feeding tube 28 is connected to the gas/liquid feeding nozzle 23.

The composite cable 25, the first to third light guide bundles 26A to 26C, the treatment instrument channel 27, and the gas/liquid feeding tube 28 are passed through the bending portion 11 and the flexible tube portion 12 to be extended to the inside of the operation portion 6. Note that the respective light guide bundles 26A to 26C are merged inside the flexible tube portion 12, and thereafter extended, as one light guide bundle 26, to the inside of the operation portion 6.

The operation portion 6 includes a treatment instrument insertion port 6a, an angle operation knob 6b, and a zoom lever 6c. The treatment instrument insertion port 6a configures a proximal end side opening portion of the treatment instrument channel 27. The angle operation knob 6b is configured to perform bending operation of the bending portion 11. The zoom lever 6c is configured to perform an operation for changing an optical characteristic of the image pickup unit 20.

The composite cable 25, the light guide bundle 26, and the gas/liquid feeding tube 28 that are extended to the inside of the operation portion 6 are inserted through the inside of the universal cord 7. The universal cord 7 includes, at the proximal end portion thereof, an endoscope connector 8 configured to be detachably connected to the control apparatus 3.

The endoscope connector 8 is configured to connect the composite cable 25, the light guide bundle 26, and the gas/liquid feeding tube 28 to the control apparatus 3.

The control apparatus 3 includes a processor such as a central processing unit (CPU), and is configured to integrally control the whole endoscope system 1. The control apparatus 3 includes an image control section 3a, a light source control section 3b, and a gas/liquid feeding control section 3c.

The image control section 3a is electrically connected to the image pickup unit 20 and the operation portion 6 through the composite cable 25. The image control section 3a receives an operation signal to the zoom lever 6c, to control the optical characteristic of an objective optical unit (to be described later) provided in the image pickup unit 20. Furthermore, the image control section 3a drives and controls the image pickup device (to be described later) of the image pickup unit 20, and converts an image pickup signal outputted from the image pickup unit 20 into an image signal. An image generated by the conversion in the image control section 3a is displayed on the display apparatus 4 such as a monitor. In the present embodiment, the control apparatus 3 includes the image control section 3a, to thereby achieve a function as an image processing apparatus.

The light source control section 3b is connected to a light source apparatus, not shown, incorporated in the control apparatus 3. The light source control section 3b drives and controls the light source apparatus, to thereby control brightness, etc., of illumination light to be supplied to the first to third illumination optical units 21A to 21C through the light guide bundle 26 (the first to third light guide bundles 26A to 26C).

The gas/liquid feeding control section 3c is connected to a gas/liquid feeding apparatus, not shown, incorporated in the control apparatus 3. The gas/liquid feeding control section 3c drives and controls the gas/liquid feeding apparatus, to thereby feed gas or liquid to the gas/liquid feeding nozzle 23 through the gas/liquid feeding tube 28.

Next, specific description will be made on the configuration of the distal end portion 10 of the above-described endoscope 2, with reference to FIGS. 2 to 7.

The distal end portion 10 includes a distal end frame 30 formed in a substantially columnar shape. The distal end frame 30 is rigid and made of metal such as stainless steel. It is preferable that the magnetization of the distal end frame 30 is reset by performing known thermal processing and the like.

A distal end cover 31, which forms the distal end surface of the distal end portion 10, is adhered and fixed to the distal end side of the distal end frame 30. In addition, the outer circumference of the distal end frame 30 is covered with an outer cover 32. Furthermore, the outer circumferential portion on the distal end side of the outer cover 32 is fixed to the distal end frame by a thread-wound adhering portion 33.

The distal end frame 30 is provided with an image pickup unit holding hole 30a. The image pickup unit 20 is inserted and fitted in the image pickup unit holding hole 30a to be fixed therein by a set screw, not shown, or the like. The distal end of the image pickup unit 20 is exposed outside the distal end cover 31, to thereby form an observation window 20a on the distal end portion 10.

Figure 4:
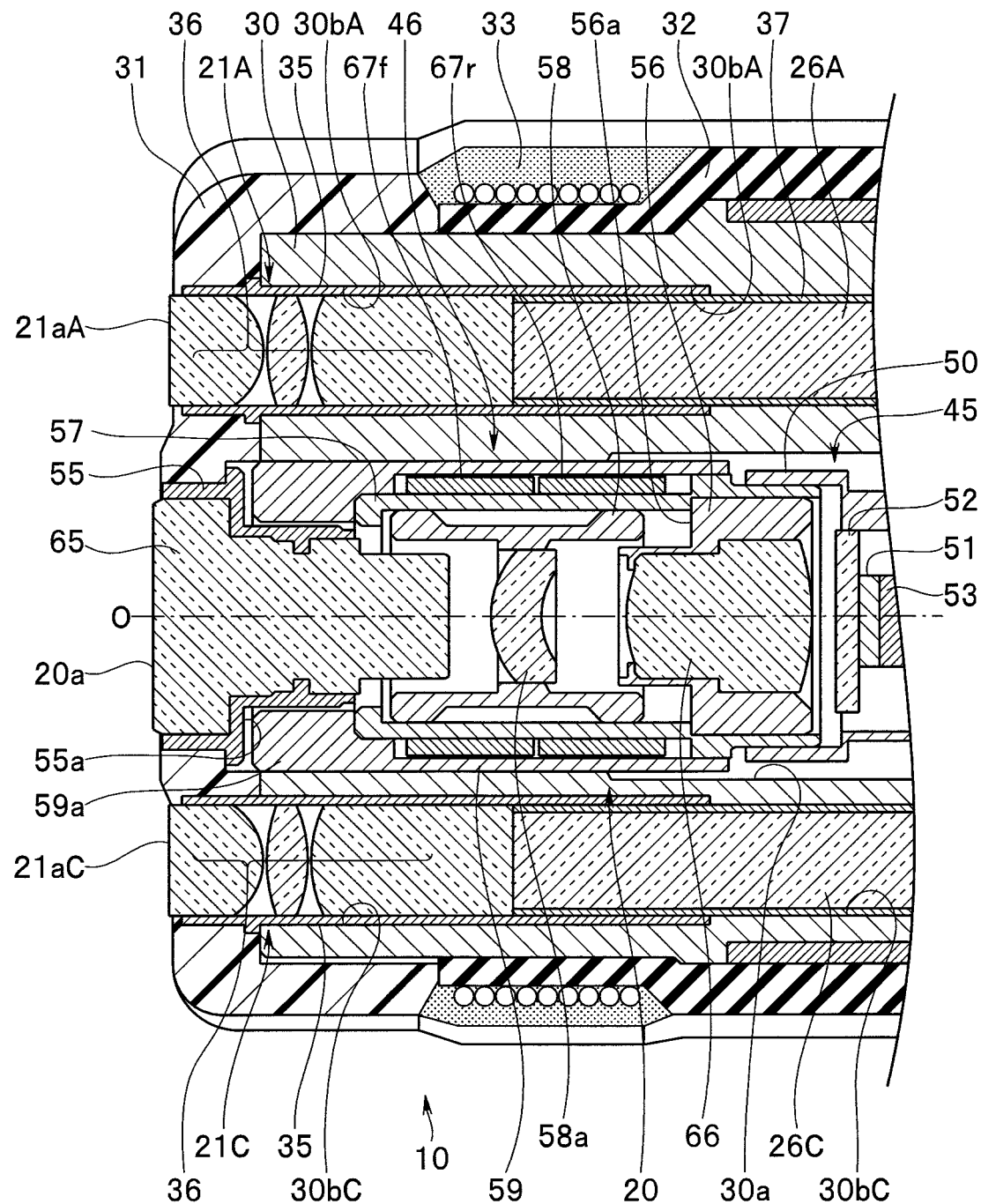
FIG. 4 is a sectional view taken along the line IV-IV in FIG. 2.

As shown in FIGS. 4 and 5, the distal end frame 30 includes a plurality of illumination optical unit holding holes (for example, three illumination optical unit holding holes: first to third illumination optical unit holding holes 30bA to 30bC) at positions surrounding the periphery of the image pickup unit 20. The first to third illumination optical units 21A to 21C are inserted and fitted respectively in the first to third illumination optical unit holding holes 30bA to 30bC.

Each of the first to third illumination optical units 21A to 21C includes an illumination lens frame 35 made of metal and formed in a substantially cylindrical shape and a plurality of lenses 36 held in the illumination lens frame 35.

The distal ends of the first to third illumination optical units 21A to 21C are exposed outside the distal end cover 31, to thereby form illumination windows 21aA to 21aC, respectively, on the distal end portion 10.

On the other hand, on the proximal end sides of the first to third illumination optical units 21A to 21C, the distal end sides of the first to third light guide bundles 26A to 26C to which light guide pipe sleeves 37 made of metal are respectively attached are inserted respectively into the first to third illumination optical unit holding holes 30bA to 30bC. The first to third light guide bundles 26A to 26C are fixed by the light guide pipe sleeves 37 being pressed respectively against the inner walls of the first to third light guide bundles 26A to 26C by set screws 38 (see FIG. 5). The respective illumination optical units 21A to 21C are thus optically connected respectively to the light guide bundles 26A to 26C, to thereby be capable of applying illumination light supplied from the control apparatus 3 to a subject.

Furthermore, as shown in FIGS. 2 and 5, the distal end frame 30 is provided with a through hole for channel 30c. The distal end of the through hole for channel 30c is open as the treatment instrument channel port 22. A pipe sleeve 40 made of metal is inserted in the through hole for channel 30c, and the distal end side of the treatment instrument channel 27 is connected to the pipe sleeve 40.

Figure 3:
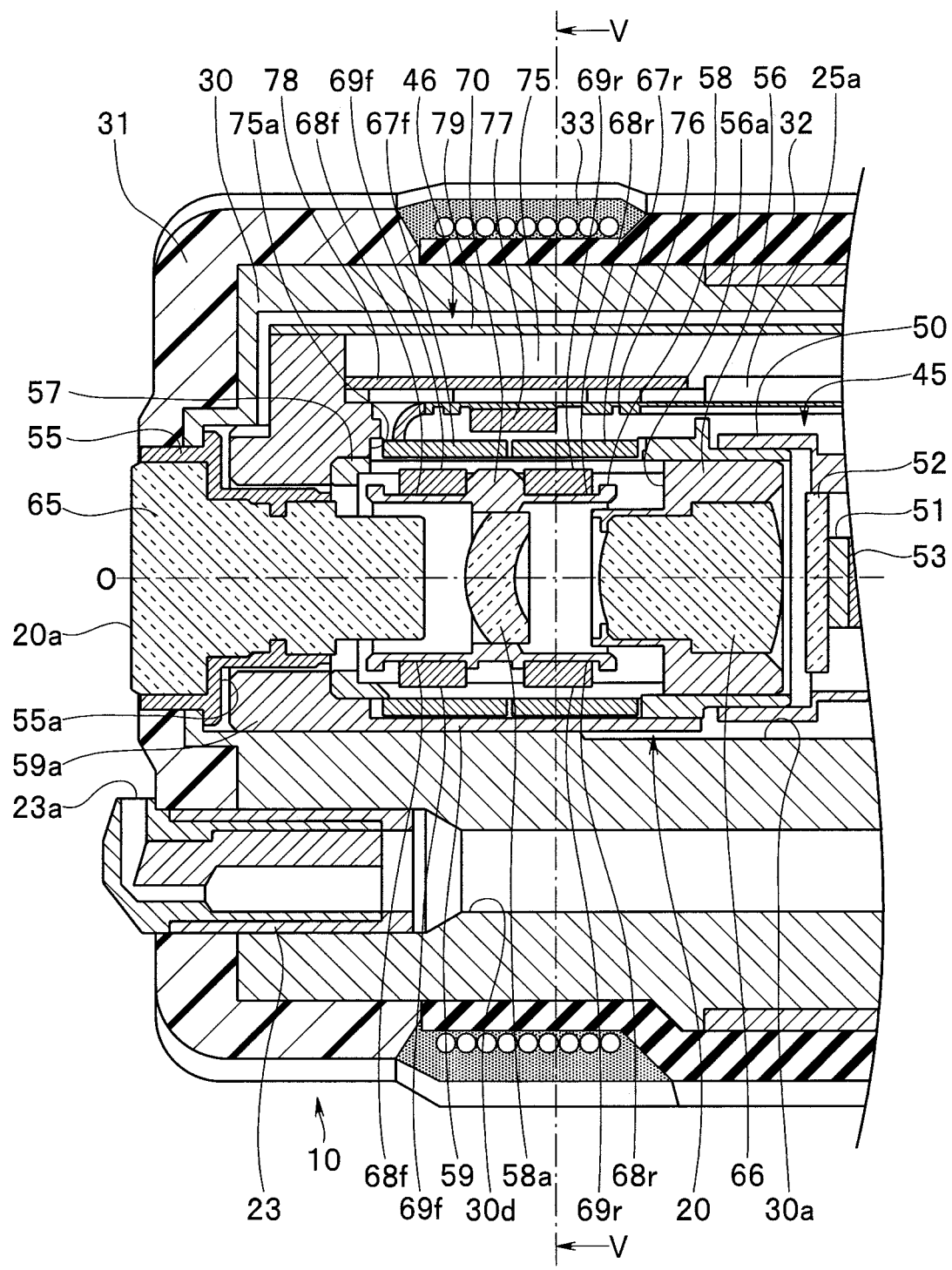
FIG. 3 is a sectional view taken along the line III-III in FIG. 2.

As shown in FIGS. 3 and 5, the distal end frame 30 includes a nozzle insertion hole 30d at a position surrounding the periphery of the image pickup unit 20. The gas/liquid feeding nozzle 23 made of metal is inserted and fitted in the nozzle insertion hole 30d. The gas/liquid feeding nozzle 23 is fixed by an adhesive, not shown, or the like, with a spouting port 23a, which is provided at the distal end of the nozzle, directed toward the observation window 20a. On the other hand, on the proximal end side of the distal end frame 30, the gas/liquid feeding tube 28 is connected to the gas/liquid feeding nozzle 23. The gas/liquid feeding nozzle 23 is capable of jetting air and cleaning water supplied from the control apparatus 3 toward the observation window 20a.

Next, description will be made on the configuration of the image pickup unit 20 provided in the distal end portion 10.

As shown in FIGS. 3 to 5, and 7, the image pickup unit 20 includes an image pickup device unit 45 and an objective optical unit 46 provided continuously with the distal end side of the image pickup device unit 45.

The image pickup device unit 45 includes an image pickup device holding frame 50. In the image pickup device holding frame 50, the front face side of a solid-state image pickup device 51 constituted of CCD, CMOS, and the like, is held through an optical member 52 such as a cover glass. An image pickup device substrate 53 is electrically connected to the rear face side of the solid-state image pickup device 51. On the image pickup device substrate 53, various control circuits and the like are mounted. Although not shown, various cables, which are branched from the composite cable 25, are electrically connected to the image pickup device substrate 53.

The objective optical unit 46 includes a front-group-lens frame 55, a rear-group-lens frame 56, a coil holding frame 57, a moving lens frame 58, and a sensor holding frame 59. The coil holding frame 57 is disposed between the front-group-lens frame 55 and the rear-group-lens frame 56. The moving lens frame 58 is a movable frame arranged slidably in the coil holding frame 57. The sensor holding frame 59 integrally holds the front-group-lens frame 55, the rear-group-lens frame 56, and the coil holding frame 57. The objective optical unit 46 is an optical unit capable of changing the optical characteristic of the objective optical system by moving the moving lens frame 58 forward and backward in a direction of an optical axis O by using a voice coil motor 60 (see FIG. 7) to be described later.

The front-group-lens frame 55 is configured of a frame body formed in a substantially cylindrical shape. The front-group-lens frame 55 is formed such that the outer diameter on the distal end side is larger than the outer diameter on the proximal end side. The outer diameter on the distal end side thus differs in size from the outer diameter on the proximal end side, to thereby form a step portion 55a at a midway part of the outer circumferential surface of the front-group-lens frame 55. The step portion 55a is set as a contact surface for positioning the front-group-lens frame 55 with respect to the sensor holding frame 59.

In addition, the front-group-lens frame 55 holds inside thereof a front-group lens 65 constituted of a plurality of fixed lenses. The front-group lens 65 constitutes the objective optical system of the objective optical unit 46.

The rear-group-lens frame 56 is configured of a frame body formed in a substantially cylindrical shape. The rear-group-lens frame 56 is formed such that the outer diameter on the distal end side is smaller than the outer diameter on the proximal end side. The outer diameter on the distal end side thus differs in size from the outer diameter on the proximal end side, to thereby form a step portion 56a at a midway part of the outer circumferential surface of the rear-group-lens frame 56. The step portion 56a is set as a contact surface for positioning the rear-group-lens frame 56 with respect to the coil holding frame 57.

In addition, the rear-group-lens frame 56 holds inside thereof a rear-group lens 66 constituted of a plurality of fixed lenses. The rear-group lens 66 constitutes the objective optical system of the objective optical unit 46.

The coil holding frame 57 is configured of a frame body formed in a substantially cylindrical shape. The coil holding frame 57 includes reduced thickness portions 57a extending in the direction of the optical axis O. The reduced thickness portions 57a are formed at four positions at 90 degree intervals around the optical axis O (see FIG. 7).

Two coils 67f, 67r constituting the voice coil motor 60 are arranged on the outer circumferential surface of the coil holding frame 57. The two coils 67f, 67r are arranged side by side in the direction of the optical axis O.

The moving lens frame 58 is configured of a frame body formed in a substantially cylindrical shape. The moving lens frame 58 holds inside thereof a moving group lens 58a constituted of one lens or two or more lenses. The moving group lens 58a constitutes the objective optical system of the objective optical unit 46.

A pair of recessed portions 68f, 68r is provided at each of four positions on the outer circumferential surface of the moving lens frame 58 so as to be located at each 90 degree point around the optical axis O. The recessed portion 68f and the recessed portion 68r in each pair are arranged side by side in the direction of the optical axis O. The recessed portion 68f and the recessed portion 68r in each pair respectively hold two magnets 69f and 69r, which constitute the voice coil motor 60, such that the two magnets are arranged side by side in the direction of the optical axis O.

Each of the magnets 69f, 69r is arranged such that a part of each of the magnets protrudes from each of the recessed portions 68f, 68r in a radially outward direction of the moving lens frame 58. In addition, each of the magnets 69f, 69r is magnetized so as to have a polarity in the thickness direction (that is, in the radial direction of the moving lens frame 58). The magnets 69f, 69r in the present embodiment are arranged respectively in the recessed portions 68f, 68r such that each magnet has an S-pole in the radially outward direction of the moving lens frame 58, and an N-pole in the radially inward direction of the moving lens frame 58, and the magnets 69f, 69r are fixed respectively to the recessed portions 68, 68r by an adhesive.

Among the four pairs of recessed portions 68f, 68r disposed on the moving lens frame 58, one pair of recessed portions 68f, 68r have a key 70 therebetween. The key 70 protrudes in the radially outward direction from between the one pair of magnets 69f, 69r arranged in the one pair of recessed portions 68f, 68r. The key 70 is inserted into any one of the four reduced thickness portions 57a when the moving lens frame 58 is inserted in the coil holding frame 57. Such insertion of the key 70 into one of the reduced thickness portions 57a restricts the rotation of the moving lens frame 58 around the optical axis O. In other words, the moving lens frame 58 is housed inside the coil holding frame 57, with the rotation around the optical axis O being restricted by the key 70 and the movement in the direction of the optical axis O being allowed.

The sensor holding frame 59 is configured of a frame body formed in a substantially cylindrical shape. The sensor holding frame 59 includes, on the inner circumference on the distal end side thereof, an inward flange 59a.

The sensor holding frame 59 includes, on one side of the outer circumferential portion thereof, a sensor holding groove 75. The sensor holding groove 75 includes, in a part on the distal end side thereof, a through hole 75a penetrating the inside and outside of the sensor holding frame 59.

A sensor substrate 76 is arranged inside the sensor holding groove 75. The sensor substrate 76 is provided with a Hall element 77 for detecting magnetic fields. The Hall element 77 is disposed on a surface facing the through hole 75a. Various cables 25a branched from the composite cable 25 are connected to the sensor substrate 76. The sensor holding groove 75 is provided with a biasing plate 78, which is configured of a metal plate, on a radially outward position with respect to the sensor substrate 76.

The sensor holding groove 75 in which the sensor substrate 76 and the biasing plate 78 are thus housed is closed by a lid body 79.

The sensor holding frame 59 holds, on the distal end side thereof, the front-group-lens frame 55. Specifically, the front-group-lens frame 55 is fixed to the sensor holding frame 59 by adhering or the like, with the proximal end side of the front-group-lens frame 55 being inserted into the sensor holding frame 59. The step portion 55a of the front-group-lens frame 55 is in contact with the distal end surface of the inward flange 59a of the sensor holding frame 59, with an adhesive, not shown, interposed therebetween. The front-group-lens frame 55 is thus positioned in the direction of the optical axis O with respect to the sensor holding frame 59.

In addition, the coil holding frame 57 is held inside the sensor holding frame 59. Specifically, the coil holding frame 57 is fixed by adhering or the like, with the distal end surface thereof being in contact with the proximal end surface of the inward flange 59a of the sensor holding frame 59.

The positioning of the coil holding frame 57 around the optical axis O is determined such that one pair of magnets 69f, 69r faces the Hall element 77. The one pair of magnets 69f, 69r is among the plurality of pairs (four pairs in the present embodiment) of magnets 69f, 69r on the moving lens frame 58 housed in the coil holding frame 57. With such a configuration, the Hall element 77 is capable of detecting a position of the moving lens frame 58 in the direction of the optical axis O based on a change in the magnetic fields received from the one pair of magnets 69f, 69r. In addition, the one pair of magnets 69f, 69r is attracted toward the biasing plate 78, to thereby suppress the backlash of the moving lens frame 58 in the coil holding frame 57. Such a configuration achieves a stable sliding performance of the moving lens frame 58 and a stable optical characteristic of the objective optical system.

Furthermore, the sensor holding frame 59 holds, inside thereof, the rear-group-lens frame 56 at a position on the proximal end side with respect to the coil holding frame 57. Specifically, the rear-group-lens frame 56 is fixed by an adhesive or the like, with the distal end side thereof being inserted in the coil holding frame 57 and the proximal end side thereof being inserted in the sensor holding frame 59. The rear-group-lens frame 56 is positioned in the direction of the optical axis O with respect to the coil holding frame 57 by the step portion being brought into contact with the proximal end surface of the coil holding frame 57.

The proximal end side of the rear-group-lens frame 56 thus held in the sensor holding frame 59 is coupled with the distal end side of the image pickup device holding frame 50. With such a configuration, an image of the subject is formed on the solid-state image pickup device 51 through the objective optical system of the objective optical unit 46.

In the endoscope system 1 thus configured, w % ben the zoom lever 6c of the endoscope 2 is operated by a user or another person, the image control section 3a of the control apparatus 3 performs energization control on the coils 67f, 67r in accordance with the operation state of the zoom lever 6c. The magnets 69f, 69r receive the magnetic fields generated in the coils 67f, 67r by the energization control, to move the moving lens frame 58 in the direction of the optical axis O. The Hall element 77 detects a change in the magnetic fields according to the movement of the moving lens frame 58 in the direction of the optical axis O by the magnets 69f, 69r, and outputs the detected change in the magnetic fields, as a feedback signal, to the image control section 3a. In response to the feedback signal, the energization of the coils 67f, 67r is feedback controlled, and the moving lens frame 58 is controlled at a position on the optical axis O in accordance with the operation state of the zoom lever 6c.

Figure 6:
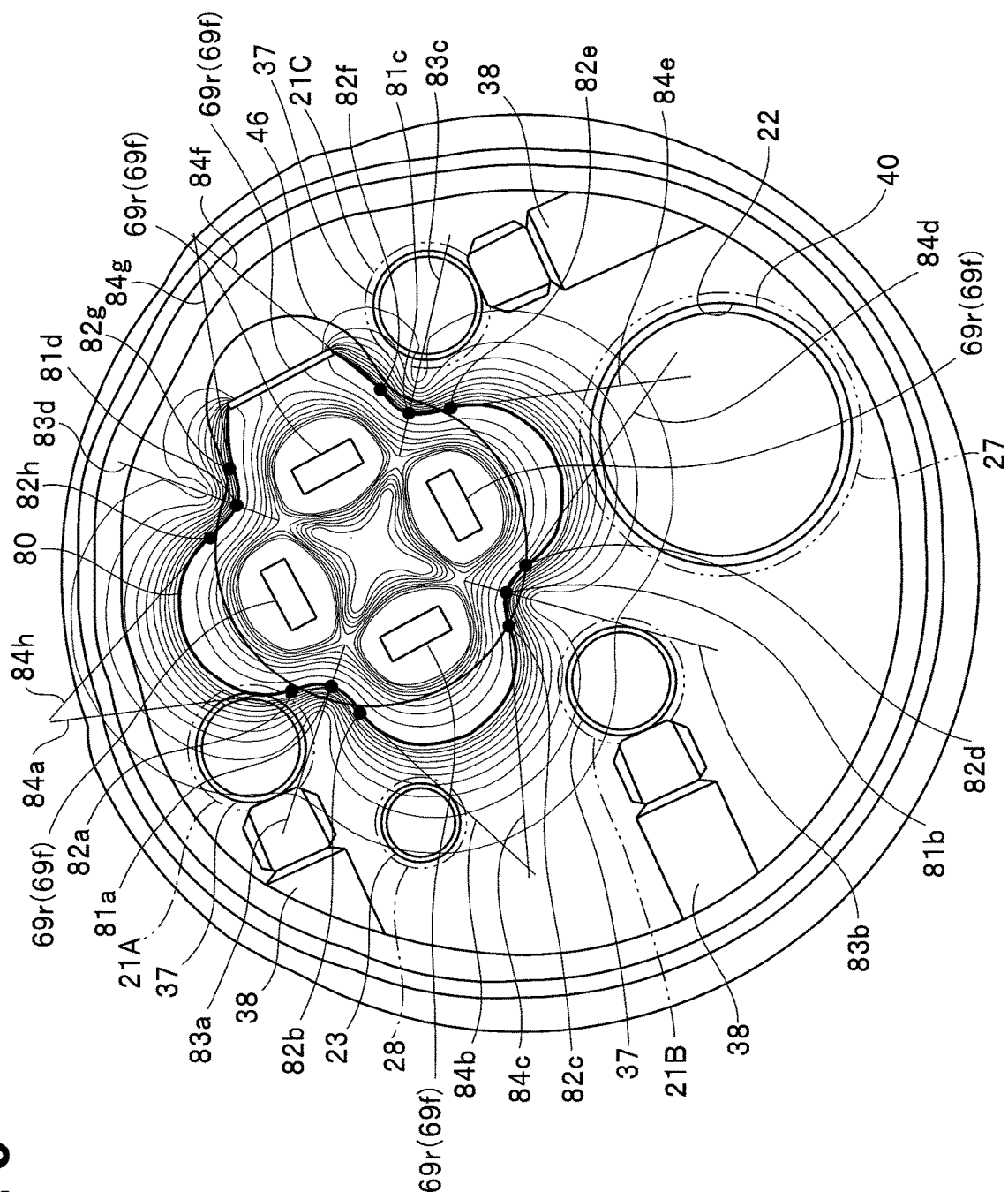
FIG. 6 is an explanatory view showing an arrangement relationship between respective internal components and magnetic fields formed by magnets of a voice coil motor.
Figure 7:
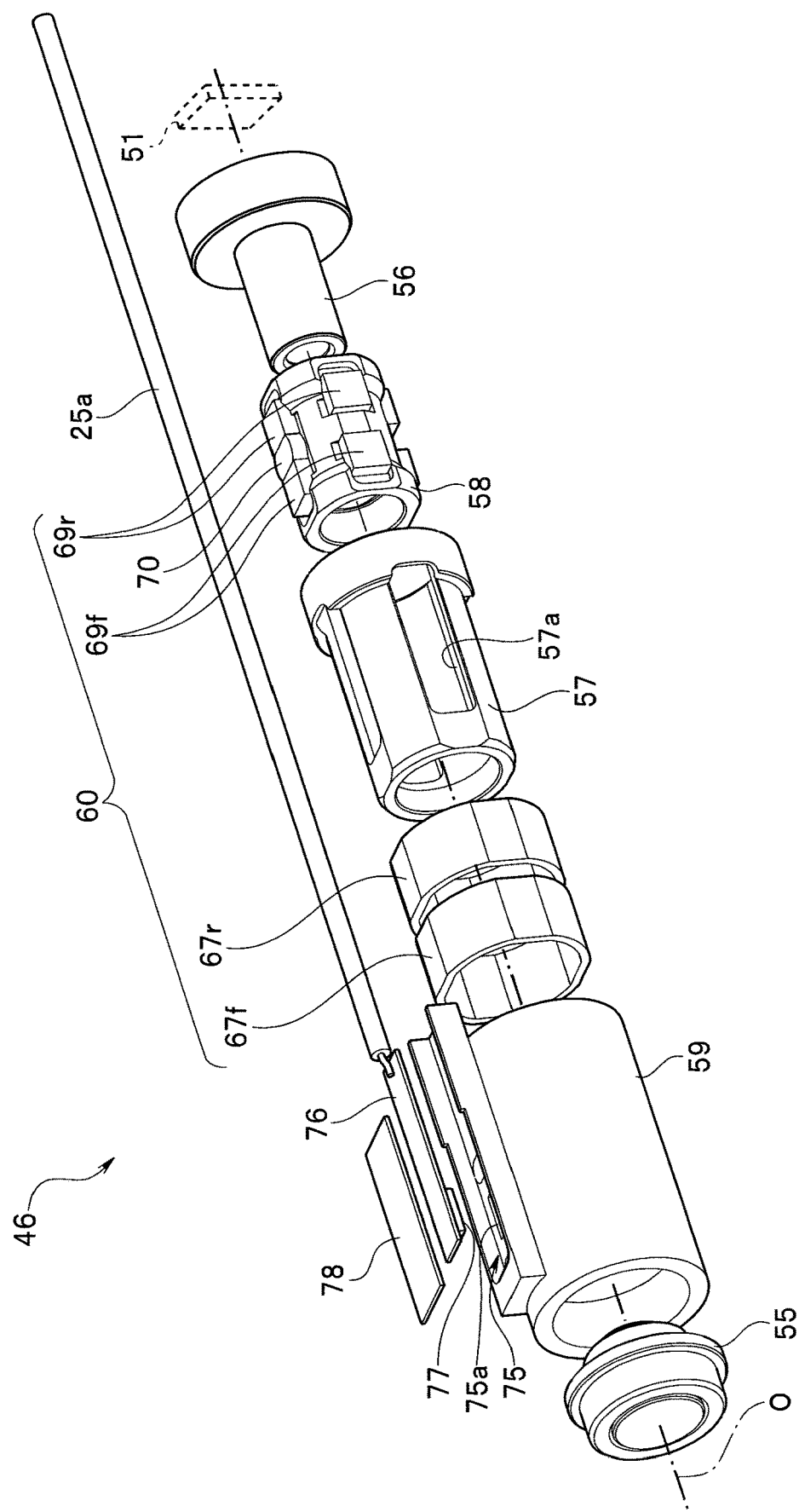
FIG. 7 is an exploded perspective view of an objective optical unit.

As shown in FIG. 6, the objective optical unit 46 of the image pickup unit 20 forms the magnetic fields around the objective optical unit 46 by the four pairs of magnets 69f, 69r. Isomagnetic lines of the magnetic fields shown in FIG. 6 indicate a distribution of the magnetic fields of the objective optical unit 46 alone before the objective optical unit 46 is incorporated in the distal end frame 30.

In order to prevent the magnetic fields from being changed due to an influence of another metal (magnetic material), various internal components are arranged in the distal end portion 10 at positions where the internal components hardly have an influence on the magnetic fields formed by the respective magnets 69f, 69r and the internal components are in the vicinity of the image pickup unit 20.

Specifically, as shown in FIG. 6, for example, the various internal components made of magnetic material are arranged so as not to substantially intrude inside a specific isomagnetic line 80 (in the present embodiment, 100 (mT), for example) set as a rough guide line. The specific isomagnetic line 80 indicates a lower limit value of the magnetic intensity which is considered to have an influence on the operating performance of the voice coil motor 60. The lower limit value is determined appropriately based on experiments, simulations, and the like, depending on the type of the objective optical unit 46. Note that even in the case where the internal components intrude inside the specific isomagnetic line 80, the intrusion can be allowed if the intruding amount is so slight as not to have an influence on the magnetic fields.

In order to bring the various internal components close to the image pickup unit 20 while satisfying the above-described condition, it is preferable that at least one of the various internal components is arranged such that at least a part thereof is located on any one of lines (first to fourth lines 83a to 83d) each connecting extreme points of valleys of the isomagnetic lines indicating different magnetic flux densities of the magnetic fields. Alternatively, it is preferable that at least one of the various internal components is arranged at a position intersecting at least one of straight lines (first to eighth straight lines 84a to 84g) each connecting one of extreme points 81a to 81d of the valleys of the specific isomagnetic line 80 and one of two inflection points located with one of the valleys positioned therebetween, among the inflection points 82a to 82h of the specific isomagnetic line 80. With such an arrangement satisfying at least one of the above-described conditions, at least one of the various internal components can be arranged along one of the valleys of the specific isomagnetic line 80, to thereby enable the internal component to be arranged as close to the objective optical unit 46 as possible, while eliminating the influence on the magnetic fields.

Here, the extreme point of each of the valleys of the isomagnetic lines refers to the extreme point of a part of each of the isomagnetic lines, the part having a shape protruding toward between one pair of magnets 69f, 69r and adjoining pair of magnets 69f, 69r. In addition, the first to fourth lines 83a to 83d each connecting the extreme points of the valleys of the respective isomagnetic lines may be approximation straight lines or may be spline curves. The four pairs of magnets 69f, 69r are arranged on the outer circumference of the moving lens frame 58 of the present embodiment. As a result, the valleys of each of the isomagnetic lines are formed respectively at four positions. Therefore, the first to fourth lines 83a to 83d each connecting the valleys of the respective isomagnetic lines are set around the objective optical unit 46. In addition, the first to eighth straight lines 84a to 84h each connecting the extreme point of one of the valleys and one of the inflection points of the specific isomagnetic line 80 are set.

In the present embodiment, the first illumination optical unit 21A is arranged at a position where at least a part thereof intersects the first line 83a. Furthermore, the first illumination optical unit 21A is arranged at a position where at least a part thereof intersects the first straight line 84a and a large part (for example, half or more of the cross-sectional area) thereof is located within a region between the two straight lines specified by the same extreme point (extreme point 81a). By satisfying these conditions, the first illumination optical unit 21A is arranged along the one of the valleys of the specific isomagnetic line 80.

Such an arrangement achieves a configuration in which the illumination lens frame 35, the light guide pipe sleeve 37 and the set screw 38, which are the various components (internal components) related to the first illumination optical unit 21A and made of magnetic material, are not arranged substantially inside the specific isomagnetic line 80, but are arranged closely to the objective optical unit 46 (image pickup unit 20).

Note that, in the present embodiment, the first illumination optical unit 21A is arranged such that a part of the illumination lens frame 35 and a part of the light guide pipe sleeve 37 intersect the specific isomagnetic line 80. However, the intrusion amount (cross-sectional area) of the illumination lens frame 35 and the light guide pipe sleeve 37 into the inside of the specific isomagnetic line 80 is so slight as not to have a great influence on the magnetic fields.

In the present embodiment, it is preferable that an intruding area Sa of the internal components, which are made of magnetic material, into the inside of the specific isomagnetic line 80 is set such that an estimated value E shown below by the equation (1) is less than a threshold Eth throughout the overall area in the direction of the optical axis O.

$$E=(Sa/S)\times P \quad (1)$$

Note that, in the equation (1), S indicates the cross-sectional area of the internal components made of magnetic material, and P indicates a magnetic permeability of the internal components made of magnetic material.

Such an arrangement enables a part of the internal components to be arranged inside the specific isomagnetic line 80 without having a great influence on the magnetic fields of the voice coil motor 60. Note that the threshold value Eth has been obtained in advance based on experiments, simulations, and the like.

The second illumination optical unit 21B is arranged at a position where at least a part thereof intersects the second line 83b. By satisfying such a condition, the second illumination optical unit 21B is arranged along one of the valleys of the specific isomagnetic line 80.

Such an arrangement achieves a configuration in which the illumination lens frame 35, the light guide pipe sleeve 37, and the set screw 38, which are the various components (internal components) related to the second illumination optical unit 21B and made of magnetic material, are not arranged substantially inside the specific isomagnetic line 80 but are arranged closely to the objective optical unit 46 (image pickup unit 20).

The third illumination optical unit 21C is arranged at a position where at least a part thereof intersects the third line 83c. By satisfying such a condition, the third illumination optical unit 21C is arranged along one of the valleys of the specific isomagnetic line 80.

Such an arrangement achieves a configuration in which the illumination lens frame 35, the light guide pipe sleeve 37, and the set screw 38, which are the various components (internal components) related to the third illumination optical unit 21C and made of magnetic material, are not arranged substantially inside the specific isomagnetic line 80 but arranged closely to the objective optical unit 46 (image pickup unit 20).

Furthermore, the gas/liquid feeding nozzle 23 is arranged at a position where at least a part thereof intersects the second straight line 84b and a large part thereof is located within a region between the two straight lines specified by the same extreme point (extreme point 81a). By satisfying these conditions, the gas/liquid feeding nozzle 23 is arranged along one of the valleys of the specific isomagnetic line 80.

Note that, in the example shown in FIG. 6, the treatment instrument channel port 22 is away from the objective optical unit 46 on the layout. Therefore, it is not especially necessary to satisfy the above-described conditions, however, if there is a need for arranging the treatment instrument channel port 22 in the vicinity of the objective optical unit 46, the treatment instrument channel port 22 is preferably arranged at a position where at least a part thereof intersecting any one of the first to fourth straight lines 84a to 84d.

According to such an embodiment, the endoscope 2 holds, in the distal end frame 30 constituting the distal end portion 10, the objective optical unit 46 and the plurality of internal components made of magnetic material and arranged around the objective optical unit 46, and the objective optical unit 46 includes the voice coil motor 60 configured to move the moving lens frame 58 forward and backward in the direction of the optical axis O by using the plurality of magnets 69f, 69r arranged on the periphery of the moving lens frame 58. In such an endoscope 2, at least one of the plurality of internal components is arranged at a position where at least a part of the at least one of the plurality of internal components intersects any one of the first to fourth lines 83a to 83d each connecting the extreme points of the valleys of the isomagnetic lines indicating the different magnetic flux densities of the magnetic fields formed by the plurality of magnets 69f, 69r. Such an arrangement ensures the operation performance of the moving lens frame 58 with an inexpensive configuration, without increasing the diameter size of the distal end portion 10.

In other words, at least one of the plurality of internal components is arranged at a position where at least a part of the at least one of the plurality of internal components intersects any one of the first to fourth lines 83a to 83d each connecting the extreme points of the valleys of the isomagnetic lines, to thereby enable the at least one internal component to be efficiently arranged along one of the valleys of the specific isomagnetic line 80. Therefore, the internal components can be arranged in the vicinity of the objective optical unit 46 while suppressing the influence of the internal components on the magnetic fields. In addition, it is possible to suppress the increase in the diameter size of the distal end portion 10. The internal components are thus arranged without having an influence on the magnetic fields. Therefore, it is not necessary to change the arrangement of the magnets 69f, 69r of the voice coil motor 60 provided in the objective optical unit 46 and the magnetic fields formed by the magnets depending on the type or the like of the endoscope 2. As a result, the operation performance of the moving lens frame 58 can be ensured with the inexpensive configuration.

In addition, at least one of the plurality of internal components is arranged at a position where at least a part of the at least one of the plurality of internal components intersects any one of the first to eighth straight lines 84a to 84h each connecting one of the extreme points 81a to 81d of the valleys of the specific isomagnetic line 80 and one of the two inflection points located with the one of the valleys positioned therebetween, among the plurality of inflection points 82a to 82h of the specific isomagnetic line 80. Also in such a case, it is possible to efficiently arrange the at least one internal component along one of the valleys of the specific isomagnetic line 80.

Note that the present invention is not limited to the above-described embodiment, but various modifications and changes are possible, and such modifications and changes are also within the technical range of the present invention.

In the above-described embodiment, description has been made on the configuration in which all the three illumination optical units 21A to 21C are arranged at the positions each intersecting any one of the first to fourth lines 83a to 83d, for example. However, the present invention is not limited to the configuration. Depending on the layout on the distal end portion 10, one or two illumination optical units can be arranged at a position or positions each intersecting any one of the first to fourth lines 83a to 83d.

In addition the number of the illumination optical units to be arranged in the distal end portion 10 is not limited to three. One or two illumination optical units, or four or more illumination optical units may be arranged.

In the above-described embodiment, description has been made on one example in which each of the illumination optical units is arranged at the position intersecting any one of the first to fourth lines 83a to 83d. However, for example, another internal component such as the treatment instrument channel port 22, the gas/liquid feeding nozzle 23, or the like, can be arranged at a position intersecting any one of the first to fourth lines 83a to 83d.

Furthermore, it is needless to say that the number of magnets constituting the voice coil motor 60 is not limited to that in the above-described embodiment.

What is claimed is:

1. An endoscope comprising:
   an objective optical unit comprising:
      a lens;
      a lens frame holding the lens; and
      an actuator configured to move the lens frame in a direction of an optical axis, the actuator including a plurality of magnets and a coil; and
   a plurality of internal components made of magnetic material and arranged around the objective optical unit,
   wherein the plurality of internal components are other than portions comprising the actuator;
   at least one of the plurality of internal components is arranged at a position where at least a part of the at least one of the plurality of internal components intersects a straight line connecting an extreme point of one of valleys of a specific isomagnetic line of magnetic fields formed by the plurality of magnets and one of two inflection points of the specific isomagnetic line, the one of the valleys positioned between the two inflection points; and
   each of the plurality of internal components are fixed relative to the lens frame.

2. The endoscope according to claim 1, wherein at least one of the plurality of internal components is arranged at a position where at least a part of the at least one of the plurality of internal components intersects one of lines each connecting extreme points of valleys of isomagnetic lines indicating different magnetic flux densities of the magnetic fields formed by the plurality of magnets.

3. The endoscope according to claim 1, wherein the plurality of internal components include an illumination optical unit and a component related to the illumination optical unit.

4. The endoscope according to claim 1, wherein the plurality of internal components include a gas/liquid feeding nozzle and a component related to the gas/liquid feeding nozzle.

5. The endoscope according to claim 1, wherein the plurality of internal components include a treatment instrument channel port and a component related to the treatment instrument channel port.

6. An endoscope system comprising:
   the endoscope according to claim 1; and
   an image processing apparatus configured to convert an image pickup signal obtained by image pickup by the endoscope into an image signal.

7. The endoscope according to claim 1, wherein the plurality of internal components comprise one or more of an illumination lens frame, a light guide pipe sleeve and a set screw.

8. The endoscope according to claim 1, wherein the actuator further comprises:
   the coil arranged around the plurality of magnets; and
   a coil frame for holding the coil, the coil frame located between the plurality of magnets and the coil.

9. An endoscope comprising:
   an objective optical unit comprising:
      a lens;
      a lens frame holding the lens; and
      an actuator connected to the lens frame, the actuator configured to move the lens frame in a direction of an optical axis, the actuator including a plurality of magnets and a coil; and
   a plurality of internal components made of magnetic material and arranged around the objective optical unit,
   wherein the plurality of internal components are other than portions comprising the actuator;
   at least one of the plurality of internal components is arranged at a position where at least a part of the at least one of the plurality of internal components intersects a straight line connecting extreme points of valleys of isomagnetic lines indicating different magnetic flux densities of magnetic fields formed by the plurality of magnets; and
   each of the plurality of internal components are fixed relative to the lens frame.

10. The endoscope according to claim 9, wherein the plurality of internal components include an illumination optical unit and a component related to the illumination optical unit.

11. The endoscope according to claim 9, wherein the plurality of internal components include a gas/liquid feeding nozzle and a component related to the gas/liquid feeding nozzle.

12. The endoscope according to claim 9, wherein the plurality of internal components include a treatment instrument channel port and a component related to the treatment instrument channel port.

13. An endoscope system comprising:
the endoscope according to claim 6; and
an image processing apparatus configured to convert an image pickup signal obtained by image pickup by the endoscope into an image signal.

14. The endoscope according to claim 9, wherein the plurality of internal components comprise one or more of an illumination lens frame, a light guide pipe sleeve and a set screw.

15. The endoscope according to claim 9, wherein the actuator further comprises:
the coil arranged around the plurality of magnets; and
a coil frame for holding the coil, the coil frame located between the plurality of magnets and the coil.

16. An endoscope comprising:
an objective optical unit held by the frame, the objective optical unit comprising:
a lens;
a lens frame holding the lens; and
an actuator connected to the lens frame, the actuator configured to move the lens frame in a direction of an optical axis, the actuator including a plurality of magnets; and
a plurality of internal components made of magnetic material and arranged around the objective optical unit,
wherein the plurality of internal components comprises one or more of an illumination lens frame, a light guide pipe sleeve and a set screw;
at least one of the plurality of internal components is arranged at a position where at least a part of the at least one of the plurality of internal components intersects a straight line connecting an extreme point of one of valleys of a specific isomagnetic line of magnetic fields formed by the plurality of magnets and one of two inflection points of the specific isomagnetic line, the one of the valleys positioned between the two inflection points; and
each of the plurality of internal components are fixed relative to the lens frame.

17. The endoscope according to claim 16, wherein the actuator further comprises:
a coil arranged around the plurality of magnets; and
a coil frame for holding the coil, the coil frame located between the plurality of magnets and the coil.

* * * * *